United States Patent [19]
Galey et al.

[11] Patent Number: 6,057,351
[45] Date of Patent: May 2, 2000

[54] COMPOUNDS OF THE 3-ARYL 2,4 DIOXO OXAZOLIDINE FAMILY AND USE THEREOF IN COSMETIC AND PHARMACEUTICALS

[75] Inventors: Jean-Baptiste Galey, Aulnay-sous-Bois; Lionel Breton, Versailles; Odile Destree, Villeparisis, all of France

[73] Assignee: Societe L'Oreal S.A., Clichy Cedex, France

[21] Appl. No.: 09/230,762

[22] PCT Filed: Jul. 11, 1997

[86] PCT No.: PCT/FR97/01289

§ 371 Date: Apr. 5, 1999

§ 102(e) Date: Apr. 5, 1999

[87] PCT Pub. No.: WO98/05654

PCT Pub. Date: Feb. 12, 1998

[30] Foreign Application Priority Data

Aug. 1, 1996 [FR] France ................................. 96 09748

[51] Int. Cl.$^7$ .......................... A61K 31/42; C07D 263/06
[52] U.S. Cl. ........................... 514/376; 548/227; 548/226
[58] Field of Search ..................................... 548/227, 226; 514/376

[56] References Cited

U.S. PATENT DOCUMENTS

| | | | |
|---|---|---|---|
| 3,703,526 | 11/1972 | Sato et al. | 548/227 |
| 3,995,049 | 11/1976 | Mangold et al. | 514/376 |
| 4,000,291 | 12/1976 | Perronnet et al. | 514/376 |
| 4,342,773 | 8/1982 | Di Toro et al. | 548/226 |
| 4,810,799 | 3/1989 | Zanker et al. | 548/226 |
| 5,100,457 | 3/1992 | Hirai et al. | 546/226 |

FOREIGN PATENT DOCUMENTS

| | | |
|---|---|---|
| 1 284 516 | of 0000 | France . |
| 2 275 206 | of 0000 | France . |
| 31 15 650 | of 0000 | Germany . |

*Primary Examiner*—Deborah C. Lambkin
*Attorney, Agent, or Firm*—Burns, Doane, Swecker & Mathis, L.L.P.

[57] ABSTRACT

Novel compounds of the aryl 2,4 dioxo oxazolidine family, a method for synthesizing same, compositions containing said compounds, and the use of an effective amount of at least one of said compounds as an active principle in a physiologically acceptable medium in a cosmetic composition or for preparing a pharmaceutical composition, are disclosed. Said compound or said compositions are useful for inducing and/or stimulating hair growth and/or controlling hair loss and/or treating hyperseborrhea and/or acne.

22 Claims, No Drawings

COMPOUNDS OF THE 3-ARYL 2,4 DIOXO OXAZOLIDINE FAMILY AND USE THEREOF IN COSMETIC AND PHARMACEUTICALS

This application is a 371 of PCT/FR97/01289 Jul. 11, 1997.

This invention relates to new compounds of the aryl 2,4 dioxo oxazolidine family. It also relates to a method for synthesizing same, compositions containing said compounds as well as the use of at least one of these compounds to induce and/or stimulate hair growth and/or control hair loss and/or treat hyperseborrhea and/or acne.

In humans, hair growth and renewal are mostly determined by the activity of the hair follicles. Their activity is cyclical and contains essentially three phases, being the anagen phase, the intermediate phase and the telogen phase.

The active anagen phase, or growth phase that lasts several years and during which the hair grows longer, is followed by a very short and temporary intermediate phase that lasts a few weeks, then by a rest phase, called telogen phase, that lasts several months.

At the end of the rest period, the hair falls out and another cycle starts up. Therefore, scalp hair renews itself permanently, and of the approximate 150 000 scalp hairs, at every moment, approximately 10% of them are resting and will therefore be replaced in a few months.

However, different causes may lead to a large loss, temporary or final, of ones hair. Alopecia is mostly due to a disturbance of the hair renewal which leads, at first, to an acceleration of the cycle frequencies at the expense of the quality of the hair then of their quantity. A progressive thinning of the hair occurs by regression of the hair called "terminal" at the fluff stage. Certain areas are hit more often, in particular the temporal and frontal gulfs in men, and in women, we notice an alopecia disseminata of the vertex.

The term alopecia covers a whole family of diseases of the hair follicle that lead to the permanent partial or general loss of hair.

In many cases, early hair loss happens to subjects who are genetically prone to hair loss and it affects men in particular. It is more particularly androgenetic or androgenic or even androgeno-genetic alopecia.

For several years, the cosmetic or pharmaceutical industry, has researched substances that will make it possible to eliminate or reduce alopecia, and in particular induce or stimulate hair growth or control hair loss.

In this regard, many active and varied compounds have already been proposed, such as for example the 3-oxide pyrimidine 6-piperidino 2,4-diamino or "Minoxidil" described in the patents U.S. Pat. Nos. 4,139,619 and 4,596,812 or yet its many derivatives such as for example those described in the requests for patents EP 0353123, EP 0356271, EP 0408442, EP 0522964, EP 0420707, EP 0459890, EP 0519819.

Nevertheless, generally speaking, it would be interesting and useful to be able to have access to active compounds other than those already known, potentially more active and/or less toxic.

This objective and others are reached through this invention which relates to new compounds that match the general formula (I):

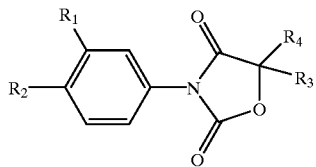

where
R1 is a halogen atom or a cyano group or an alkyl group, in $C_1$–$C_4$ substituted by at least one halogen atom;
R2 is a cyano group or a halogen atom or an alkyl carboxylate in $C_1$–$C_4$;
R3 is a hydrogen atom or an alkyl group, in $C_1$–$C_4$, possibly substituted by at least one halogen atom;
R4 is an aryl or alkyl group en $C_1$–$C_4$, substituted by at least one halogen atom or one aryl group, possibly substituted by one or several halogen atoms, by one or several carboxylic, cyano or perfluoroalkyl groups.

The invention also relates to optical isomers, alone or in a mixture in all percentages, acylated forms or even pharmaceutically acceptable salts of these compounds.

By halogen atoms we mean preferably as set forth in the invention, fluorine, chlorine or bromine atoms.

By alkyl group in $C_1$–$C_4$, we mean preferably as set forth in the invention the linear or ramified alkyl radicals in $C_1$–$C_4$, and in particular the methyl, ethyl, propyl, isopropyl, butyl, isobutyl or tertiobutyl radicals and more specifically the methyl radical.

By alkyl radical substituted by at least one halogen atom we mean preferably the radicals described above for which at least one hydrogen atom is substituted by a halogen atom, including the perhalogenated radicals for which all hydrogen atoms are replaced by as many halogen atoms.

Preferably, the alkyl radicals that are substituted by at least one halogen atom are substituted by at least one fluorine atom. The perhalogenated radicals are preferably perfluorinated radicals, in particular perfluoromethyl radicals.

By aryl radical, we mean preferably as set forth in the invention, the aromatic or heteroaromatic radicals, in particular the phenyl, pyridyl, pyrimidyl, indolyl, benzofuranyl or naphthyl radicals.

According to a particular means of preparation of the invention, R1 is preferably a chlorine atom.

According to a particular method of preparation of the invention, R1 is a perfluorinated methyl radical.

When R2 is a halogen atom, R2 is preferably a chlorine atom.

Preferably, R3 is a perfluorinated methyl radical.

Advantageously, R4 is a methyl radical possibly substituted by at least one halogen atom, preferably a perfluorinated methyl radical.

When R4 can be an aryl group, it is preferably a phenyl radical, possibly substituted.

R3 and R4 can be identical but preferably, R3 and R4 have different meanings.

As compounds matching formula (I), we can name:
the 4-(5-methyl-2,4-dioxo-5-trifluoromethyl)-oxazolidin-3-yl)-2-trifluoromethylbenzonitrile,
the 4-(5-methyl-2,4-dioxo-5-phenyl)-oxazolidin-3-yl)-2-trifluoromethylbenzonitrile,
the 4-(5-methyl-2,4-dioxo-5-trifluoromethyl)-oxazolidin-3-yl)-2-cyanobenzonitrile,
the ethyl ester of the 4-(5-methyl-2,4-dioxo-5-trifluoromethyl)-oxazolidin-3-yl)-2-cyanobenzoic acid Among these compounds, we prefer in particular:
the 4-(5-methyl-2,4-dioxo-5-trifluoromethyl)-oxazolidin-3-yl)-2-trifluoromethylbenzonitrile.

A second objective of the invention is a procedure for the preparation of compounds matching formula (I) as described above.

This procedure is characterized by the fact that we make an appropriate anhydrous solvent react in the presence of an amino, an isocyanate substituted in 3, 4 matching the general formula:

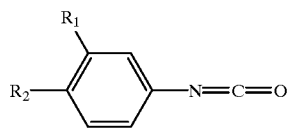

and a cyanydrine matching the general formula

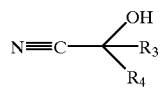

where R1, R2, R3 and R4 correspond to the definitions given previously. As an anhydrous solvent, we can use tetrahydrofuran (THF) or toluene. As an amino we can use triethylenediamine, triethylamine, 4-methylmorpholine or even pyridine.

The mixture obtained is then treated in an acid medium in the presence of alcohol, in order to eliminate the remaining excess of isocyanate residues. This acid medium can for example consist of a hydrochloric acid and methanol mixture.

The aryl derivative 2,4-dioxo oxazolidine formed is extracted using an organic solvent such as dichloromethane or ethyl acetate, then dried and lastly purified by chromatography through a silica column (Patton, T. L. J. Org. Chem. (1987) 32 (2), 383–388).

An example of preparation of the compounds as set forth in the invention is given later in the examples.

A third goal of the invention relates to cosmetic or pharmaceutical compositions, in particular dermatologic compositions, that contain at least one of the compounds matching formula (I) as defined above.

Of course, the compositions as set forth in the invention can contain the compounds matching formula (I) alone or in mixtures in all percentages.

The quantity of compounds matching formula (I) contained in the compositions of the invention depend of course on the effect sought and may therefore vary to a large degree.

To give an idea of the range, if the composition is a cosmetic composition, it may contain at least one compound matching formula (I) in a quantity representing from 0.001% to 10% of the total weight of the composition and preferably in a quantity representing from 0.01% to 5% of the total weight of the composition.

To give an idea of the range, if the composition is a pharmaceutical composition, it may contain at lease one compound matching formula (I) in a quantity representing from 0.005% to 20% of the total weight of the composition, and preferably in a quantity representing from 0.05% to 10% of the total weight of the composition.

The composition may be ingested, injected or applied on the skin (on any cutaneous area of the body), the hair, the nails or the mucosal (buccal, jugal, gingival, genital, conjunctiva). Based on the method of administration, the composition as set forth in the invention can be in all galenic forms used traditionally.

For a topical application on the skin the composition may among others, have the form of an aqueous solution, an oil solution or a dispersion solution of the lotion or serum type, the form of emulsions of liquid or semi-liquid consistency of the milk type obtained by dispersion of a fatty phase in an aqueous phase (H/E) or inversely (E/H), or the form of suspensions or emulsions of soft consistency of the cream or aqueous or anhydrous gel type, or even the form of microcapsules or microparticles, or vesicular dispersions of the ionic and/or non ionic type. These compositions are prepared according to the traditional methods.

They may also be used for scalp hair in the form or aqueous, alcoholic or hydroalcoholic solutions, or in the form of creams, gels, emulsions, mousses or even in the form of compositions for aerosol use including also a propellant under pressure. The composition as set forth in the invention may also be a composition for hair care, and, in particular, a shampoo, a lotion for hair waving, a treatment lotion, a styling cream or gel, a composition of dyes (in particular oxidation dyes) possibly in the form of coloring shampoos, conditioning lotions for the hair, a perm composition (in particular for a first phase of a perm), an anti hair loss lotion or gel, an antiparasitic shampoo, etc.

For the injection, the composition may be in the form of an aqueous or oil lotion or in the form of a serum. For the eyes, it may be in the form of drops and for ingestion, it may be in the form of capsules, syrup granules or tablets.

The quantities of the various constituents of the compositions as set forth in the invention are those used traditionally in the fields being considered.

The compositions as set forth in the invention may also consist of solid preparations that make soaps or cleansing cakes.

The compositions may also be conditioned in the form of a composition for aerosols containing also a propellant under pressure.

When the composition is an emulsion, the percentage of the fatty phase can range from 5% to 80% by weight, and is preferably between 5% and 50% by weight in relation to the total weight of the composition. The oils, waxes, emulsifiers and coemulsifiers used in the composition in the form of emulsion are chosen from among those used traditionally in the cosmetic field. The emulsifier and coemulsifier are present in the composition at a percentage ranging from 0.3% to 30% by weight, and preferably from 0.5 to 20% by weight in relation to the total weight of the composition. Furthermore, the emulsion may contain lipidic vesicles.

When the composition is an oil solution or gel, the fatty phase may represent more than 90% of the total weight of the composition.

As known, the cosmetic composition may also contain the adjuvants commonly used in the cosmetic field, such as hydrophilic or lipophilic gelling agents, hydrophilic or lipophilic additives, preservatives, antioxidants, solvents, perfumes, charges, filters, odor absorbers and colorants. The quantities of these various adjuvants are those used traditionally in the cosmetic field, and for example range from 0.01% to 10% of the total weight of the composition. These adjuvants, based on their nature, may be introduced in the fatty phase, in the aqueous phase and/or in the lipidic spherules.

The oils and waxes used in the invention can include mineral oils (white mineral oil), vegetable oils (liquid fraction of karite butter, sunflower oil), animal oils (perhydrosqualene), synthetic oils (purcelin oil), siliconized oils or waxes (cyclomethicone) and fluorinated oils (perfluoropolyethers), bees wax, carnauba wax or paraffin wax. To these oils we can add fatty alcohols and fatty acids (stearic acid). The emulsifiers used in the invention can for example include glycerol stearate, polysorbate 60 and the PEG-6/PEG-32/Glycol Stearate mixture sold by Gattefosse under the name Tefose$^R$ 63.

The solvents that can be used in the invention may include the inferior alcohols, in particular ethanol and isopropanol, glycol propylene.

The hydrophilic gelling agents that can be used in the invention may include carboxyvinyl polymers (carbomer), acrylic copolymers such as acrylate/alkylacrylate copolymers, polyacrylamides, polysaccharides such as hydroxypropylcellulose, natural gums and clays and as lipophilic gelling agents, we can name the modified clays such as bentones, fatty acid metallic salts such as aluminum stearates and ethyl cellulose, polyethylene, hydrophobic silica.

The composition may contain other hydrophilic actives such as proteins or protein hydrolysates, amino acids, polyls, urea, allantoin, sugars and sugar derivatives, hydrosoluble vitamins, vegetable extracts and hydroxyacids.

As lipophilic actives, we may use retinol (vitamin A) and its derivatives, tocopherol (vitamin E) and its derivatives, essential fatty acids, ceramides, essential oils, salicylic acid and its derivatives.

As set forth in the invention, the composition may associate at least one compound matching formula (I) with other active agents. Among these active agents, we can name as examples:—the agents that improve the activity of the regrowth and/or the reduction of hair loss and were already described for this activity as for example the nicotinic acid esters, of which in particular tocopherol nicotinate, benzyl nicotinate and alkyl nicotinates in $C_1$–$C_6$ such as methyl or hexyl nicotinates, pyrimidine derivatives, such as the 2,4-diamino 6-peperidinopyrimidine 3-Oxide or "Minoxidil" described in the patents U.S. Pat. Nos. 4,139,619 and 4,596,812, the agents that favor the regrowth of hair as those described by the applicant in the request for European patent published under number 0648488;

the agents that reduce the cutaneous differentiation and/or proliferation and/or pigmentation such as retinoic acid and its isomers, retinol and its esters, vitamin D and its derivatives, estrogens such as estradiol, kojic acid or hydroquinone;

the antibacterial agents such as clindamycin phosphate, eythromycin or antibiotics of the tetracycline group;

the antiparasitic agents, in particular metronidazole, crotamiton or pyrethroids;

the antifungal agents, in particular the compounds that belong to the imidazole group such as econazole, ketoconazole or miconazole or their salts, the polyene compounds, such as amphotericin B, the compounds of the allylamine family, such as terbinafine or even octopirox;

the antiviral agents such as acyclovir;

the steroid anti-inflammatory agents, such as hydrocortisone, betamethasone valerate or clobetasol propionate, or the non steroid anti-inflammatory agents such as for example ibuprofen and its salts, diclofenac and its salts, acetyl salicylic acid, acetaminophen or glycyrrhizic acid;

the anesthetic agents such as lidocain hydrochlorate and its derivatives;

the antipruritic agents, such as thenaldine, trimeprazine or cyproheptadine;

the keratolytic agents such as α- and β-hydroxycarboxylic or β-cetocarboxylic acids, their salts, amides or esters and more particularly the hydroxyacids such as glycolic acid, lactic acid, salicylic acid citric acid and in general fruit acids, and the n-octanoyl-5-salicylic acid;

the free antiradical agents, such as the α-tocopherol or its esters, the superoxide dismutases, certain metal chelating agents or the ascorbic acid and its esters;

the antiseborrheic agents such as progesterone;

the anti-dandruff agents such as octopirox or zinc pyrithione;

the anti-acne agents such as retinoic acid or benzoyl peroxide;

the extracts of vegetable or bacterial origin.

To the above-mentioned list, other compounds may also be added, such as for example, Diazoxide, Sprioxazone, phospholipids such as licethin, linoleic and linolenic acids, salicylic acid and its derivatives described in the French patent FR 2 581 542, as the derivatives of salicylic acid that carry an alkanoyl group with 2 to 12 atoms of carbon in position 5 of the benzene ring, hydroxycarboxylic or cetocarboxylic acids and their esters, lactones and their matching salts, anthralin, carotenoids, eicosatetrayenoic and eicosatriyenoic acids or their esters and amides, vitamin D and its derivatives, extracts of vegetable or bacterial origin.

Thus, according to a specific method, the composition as set forth in the invention also contains at least one agent chosen from among the antibacterial, antiparasitic, antifungal, antiviral, anti-inflammatory, antipruritic, anesthetic, deratolytic, free anti-radical, anti-seborrheic, anti-dandruff, and anti-acne agents and the agents that reduce the cutaneous differentiation and/or proliferation and/or pigmentation, the extracts of vegetable or bacterial origin.

We can also consider that the composition that contains at least one compound as defined previously be in the form of a liposome, in particular as described in the request for patent WO 94/22468 filed on Oct. 13, 1994 by Anti Cancer Inc., the compound encapsulated in the liposomes can be delivered selectively at the level of the hair follicle.

The pharmaceutical composition as set forth in the invention can be administered by parenteral, enteral or yet by topical pathway. Preferably, the pharmaceutical composition is administered by topical pathway.

A fourth goal of the invention relates to the use as an active principle, in an acceptable physiological medium, in a cosmetic composition or for the preparation of a pharmaceutical composition, of an effective quantity of at least one compound matching formula (I) described above.

The compounds matching formula (I) are indeed excellent potassic canal openers, the main property of Minoxidil, the only compound known to date as being effective in the treatment of hair loss.

They are also excellent androgen receiving antagonists, the androgens being responsible for a particularly widespread form of alopecia, the androgen-dependant alopecia. But, we also know that the androgens are involved in hyperseborrhea and acne.

Thus the compounds matching formula (I) present remarkable activities that justify their use as medication, in particular to induce and/or stimulate hair growth and/or control hair loss and/or in the treatment of hyperseborrhea and/or acne.

To the knowledge of the applicant, never before has the use of such mixed activity, potassic canal openers/anti-androgen compounds of the aryl 2,4 dioxo oxazolidine family been proposed for fighting hair loss and/or for the treatment of hyperseborrhea and/or acne.

Thus, the goal of the invention is the use as an active principle in an acceptable physiological medium, in a cosmetic composition or for the preparation of a pharmaceutical composition, of an effective quantity of at least one compound matching formula (I), this compound or the compositions being intended to induce and/or stimulate the growth of hair and/or control hair loss and/or treat hyperseborrhea and/or acne.

Preferably, the compound used as set forth in the invention is chosen from:

the 4-(5-methyl-2,4-dioxo-5-trifluoromethyl)-oxazolidin-3-yl)-2-trifluoromethylbenzonitrile, the 4-(5-methyl-2,4-dioxo-5-phenyl)-oxazolidin-3-yl)-2-trifluorometylbenzonitrile, the 4-(5-methyl-2,4-dioxo-5-trifluoromethyl)-oxazolidin-3-yl)-2-cyanobenzonitrile;

the ethyl ester of the 4-(5-methyl-2,4-dioxo-5-trifluoromethyl)-oxazolidin-3-yl)-2-cyanobenzine acid.

Among these compounds, we prefer in particular:

the 4-(5-methyl-2,4-dioxo-5-trifluoromethyl)-oxazolidin-3-yl)-2-trifluoromethylbenzonitrile.

Of course, the compounds may be used alone of in mixtures.

The cosmetic composition as set forth in the invention is to be applied on the alopecic areas of an individual's scalp and scalp hair, it can be left in contact for several hours and is eventually rinsed off. One can, for example, apply the composition containing an effective quantity of at least one compound as defined previously, at night, leave it on overnight and then shampoo it off in the morning. These applications may be renewed daily for one or several months depending on the individual.

Thus, another goal of this invention is a cosmetic treatment for scalp hair and/or the scalp and/or the skin, characterized by the fact that it consists in applying a cosmetic composition containing an effective quantity of at least one compound as defined previously to the hair and/or the scalp and/or the skin, in leaving said composition in contact with the hair and/or the scalp and/or the skin, and then rinsing it off.

The treatment procedure has the characteristics of a cosmetic procedure to the extent that it allows for the improvement of the hair and/or skin's appearance by giving them greater strength and a better look.

We will now illustrate with examples that could not in any way restrict the scope of the invention.

EXAMPLE 1

4-(5-methy-2,4-dioxo-5-trifluoromethyl)-oxazolidin-3-yl)-2-trifluoromethylbenzonitrile synthesis 1.09 g of 4-isocyanato 2-trifluoromethyl benzonitrile is dissolved in 20 ml of anhydrous THF. 150 µl of Triethylamine is added, followed by 860 mg of cyanohydrine trifluoroacetone in solution in 10 ml of anhydrous THF. The reaction medium is agitated for 2 hours at room temperature.

5 ml of methanol is added, then, after 30 min., 10 ml of hydrochloric acid 1N is added. After 2 hours at room temperature, 20 ml of water is added. The reaction medium is extracted by 4×25 ml of dichloromethane. The organic phase is washed in 25 ml of water, dried over sodium sulfate, evaporated to dryness. The residue obtained is purified by chromatography through a silica column, and dichloromethane is the eluent. We obtain 540 mg of a white precipitate.

Analyses

*RMN Spectrum 500 MHz in $CDCl_3$: consistent with the structure

*Ultimate analysis:

|  | C | H | N | F |
|---|---|---|---|---|
| % calc | 44.32 | 1.70 | 7.95 | 32.38 |
| % Tr | 44.52 | 1.76 | 8.00 | 32.53/32.24 |

*Melting point: Kofler=90–92° C.

EXAMPLE 2

Measuring the affinity of the 4-(5-methyl-2,4-dioxo-5-trifluoromethyl)-oxazolidin-3-yp)-2-trifluoromethylbenzonitrile for the androgen receiver.

These measurements of receiving affinity for the androgen receiver are executed according to the Schilling and Liao method, described in "The Prostate", 1984, 5.p. 581–588.

The compound is tested at several concentrations. During the experiment, the reference molecule(mibolerone) is tested at the same time at 8 concentrations in order to validate the experiment.

| Compound at the concentration of: | 0.1 µM | 1 µM | 10 µM |
|---|---|---|---|
| 4-(5-methyl-2,4-dioxo-5-trifluoromethyl)-oxazolidin-3-yl)-2-trifluoromethylbenzonitrile | 2 | 17 | 56 |

The results are expressed in % of inhibition of the fixation of the testosterone on its receiver. The internal reference (mibolerone) inhibits up to 50% of this fixation at a concentration of 4.3 nM.

EXAMPLE 3

Measurement of the "potassic canal opener" type activity of the 4-(5-methyl-2,4-dioxo-5-trifluoromethyl)-oxazolidin-3-yl)-2-trifluoromethylbenzonitrile by measuring in vitro the relaxing power of the molecules of thoracic aorta rings.

The experiments are carried out according to the Newgreen et al (Br. J. Pharmacol., 100, 1990, p. 605–613), Bray et al (Arch. Pharmacol., 344, 1991, p. 351–359) and Wickerden et al (Br. J. Pharmacol., 103, 1991, 1148–1152) methods.

After placing the tissues in the isolated organ tanks, they (smooth aortic muscles) are subjected to an initial tension of 2 g.

After a period of equilibration, the tissues are exposed to a potassium chloride solution (KCl, at 20 mM) in order to obtain a sustained contractile response. After stabilization of this contractile response, the relaxing activity (of the potassic canal opener type) of the molecules to be tested is evaluated in response doses.

During the experiment, two reference molecules are used: cromakalim and Minoxidil.

| Compound at the concentration of: | 0.1 µM | 1 µM | 10 µM |
|---|---|---|---|
| 4-(5-methy-2,4-dioxo-5-trifluoromethyl)-oxazolidin-3-yl)-2-trifluoromethylbenzonitrile | 12 | 69 | 95 |
| Minoxidil | 25 | 65 | 95 |
| Cromakalim | 46 | 86 | 100 |

Results expressed in % of inhibition of the contraction provoked by the KCl at 20 mM. The results show that the 4-(5-methyl-2,4-dioxo-5-trifluoromethyl)-oxazolidin-3-yl)-2-trifluoromethylbenzonitrile has a mixed activity, with a preferred activity for the K* Agonist facet.

EXAMPLE 4

Examples of compositions containing a 2,4 dioxo oxazolidine aryl. These compositions are obtained by the usual techniques traditionally used in the cosmetic and pharmaceutical fields.

| Niosomized gel | | |
|---|---|---|
| Chimexane NS © | | 1.800 g |
| Monosodic stearoylglutamate | | 0.200 g |
| Compound from example 1 | | 1.000 g |
| Carbomer | | 0.200 g |
| Triethanolamine | qs pH = 7 | |
| Preservatives | qs | |
| Perfumes | qs | |
| Demineralized water | qsp | 100.000 g |

This gel is applied to the scalp, once or twice a day.

| Anti hair loss lotion | | |
|---|---|---|
| Compound from example 1 | | 2.000 g |
| Glycol propylene | | 30.000 g |
| Ethyl alcohol | | 40.500 g |
| Water | qsp | 100.000 g |

This lotion is applied to the scalp, once or twice a day, in doses of 1 ml per application.

| Thickened anti hair loss lotion | | |
|---|---|---|
| Compound from example 1 | | 0.500 g |
| Kawaine | | 2.000 g |
| Hydroxypropylcellulose (Hercules' Klucel G) | | 3.500 g |
| Ethyl alcohol | qsp | 100.000 g |

This thickened lotion is applied to the scalp, once or twice a day, in doses of 1 ml per application.

| Niosomized lotion | | |
|---|---|---|
| Chimexane NL © | | 0.475 g |
| Cholesterol | | 0.475 g |
| Monosodic stearoylglutamate | | 0.050 g |
| Compound from example 1 | | 0.500 g |
| Preservatives | qs | |
| Colorants | qs | |
| Perfume | qs | |
| Demineralized water | qsp | 100.000 g |

This lotion is applied to the scalp, once or twice a day, in doses of 1 ml per application

| Anti hair loss lotion | | |
|---|---|---|
| Compound from example 1 | | 0.050 g |
| Propyleneglycol monomethylether (Dow Chemical's Dowanol PM) | | 20.000 g |

| Anti hair loss lotion | | |
|---|---|---|
| Hydroxypropylcellulose (Hercules' Klucel G) | | 3.000 g |
| Ethyl alcohol | | 40.000 g |
| Minoxidil | | 2.000 g |
| Water | qs | 100.000 g |

This thickened lotion is applied to the scalp, once or twice a day, in doses of 1 ml per application.

| Anti hair loss lotion | | |
|---|---|---|
| Compound from example 1 | | 2.000 g |
| Glycol propylene | | 10.000 g |
| Isopropyl alcohol | qsp | 100.000 g |

This lotion is applied to the scalp, once or twice a day.

With each of the compositions described in the examples above, we noticed, after several months of treatment, based on the subjects being treated, a slowing-down of the hair loss and/or a regrowth effect.

What is claimed is:

1. A compound matching formula (I):

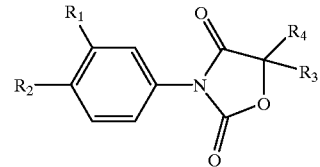

where:
R1 is a halogen atom or a cyano group or an alkyl group, $C_1$–$C_4$, substituted by at least one halogen atom;
R2 is a cyano group or a halogen atom, or an alkyl carboxylate $C_1$–$C_4$;
R3 is a hydrogen atom or an alkyl group, $C_1$–$C_4$, optionally substituted by at least one halogen atom,
R4 is an alkyl group, $C_1$–$C_4$, substituted by at least one halogen atom or one aryl group, optionally substituted by one or several halogen atoms, by one or several carboxylic, cyano or perfluoroalkyl groups;
or its optical isomers, alone or mixed in all percentages, or even its pharmaceutically accepted salts.

2. A compound as set forth in claim 1, wherein R1 is a chlorine atom.

3. A compound as set forth in claim 1, wherein R1 is a perfluorinated methyl radical.

4. A compound as set forth in claim 1 wherein R2 is a fluorine atom.

5. A compound as set forth in claim 1 wherein R3 is a perfluorinated methyl radical.

6. A compound as set forth in claim 1 wherein R4 is a methyl radical possibly substituted by at least one halogen atom.

7. A compound as set forth in claim 1 wherein R4 is a phenyl radical possibly substituted.

8. A compound as set forth in claim 1 wherein the compound comprises:
the 4-(5-methyl-2,4-dioxo-5-trifluoromethyl)-oxazolidin-3-y)-2-trifluoromethylbenzonitrile,
the 4-(5-methyl-2,4-dioxo-5-phenyl)-oxazolidin-3-yl)-2-trifluoromethylbenzonitrile, the 4-(5-methyl-2,4-dioxo-5-trifluoromethyl-oxazolidin-3-yl)-2-cyanobenzonitrile, or the ethyl ester of the 4-(5-methyl-2,4-dioxo-5-trifluoromethyl)-oxazolidin-3-yl)-2-cyanobenzoic acid.

9. A preparation method of a compound corresponding to formula (I) as defined in claim 1, wherein in an appropriate anhydrous solvent, comprising reacting an isocyanate substituted in 3, 4 corresponding to the formula:

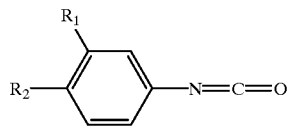

and a cyanydrine matching the formula

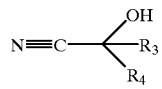

where R1, R2, R3 and R4 have the same definitions as above in the presence of an amino, treating the mixture thus obtained with an acid in the presence of alcohol and the 2,4-dioxo oxazolidine aryl derivative created is extracted using an organic solvent, dried then purified by chromatography through a silica column.

10. A procedure as set forth in claim 9, wherein the anhydrous solvent is tetrahydrofuran.

11. A procedure as set forth in claim 9 wherein the amino is triethylamine.

12. A procedure as set forth in claim 9 wherein the mixture obtained is treated by a mixture of hydrochloric acid and methanol.

13. A procedure as set forth in claim 9 wherein the organic solvent is dichloromethane.

14. A composition containing at least one compound corresponding to formula (I) as defined in claim 1.

15. A composition as set forth in claim 14, which is intended for cosmetic or pharmaceutical use and comprises a cosmetically or pharmaceutically acceptable carrier therefor.

16. A cosmetic composition as set forth in claim 15, wherein contains at least one compound corresponding to formula (I) in a quantity representing from 0.001% to 10% of the total weight of the composition.

17. A pharmaceutical composition as set forth in claim 14 which contains at least one compound corresponding to formula (I) in a quantity representing from 0.005% to 20% of the total weight of the composition.

18. A composition as set forth in claim 14, the which also contains at least one agent comprising anti-bacterial, anti-parasitic, anti-fungal, anti-viral, anti-inflammatory, antipruritic agents, anesthetics, keratolytics, free anti-radicals, anti-seborrheic, anti-dandruff, anti-acne agents and/or agents that reduce the cutaneous differentiation and/or proliferation and/or pigmentation, extracts of vegetable or bacterial origin.

19. A composition as set forth in claim 14, which intended to induce and/or stimulate the growth of hair and/or control hair loss and/or treat hyperseborrhea and/or acne.

20. The compounds corresponding to formula (I):

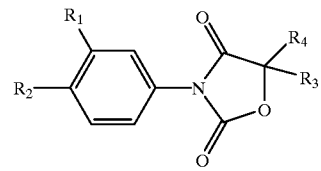

as defined in claim 1.

21. A cosmetic composition or a pharmaceutical composition, comprising an effective quantity of at least one compound corresponding to formula (I) according to claim 1 to induce and/or stimulate the growth of hair and/or control hair loss and/or treat hyperseborrhea and/or acne.

22. A cosmetic treatment procedure for scalp hair and/or the scalp, comprising applying a cosmetic composition as defined in claim 14, to the hair and/or the scalp and/or the skin of an individual in need of such treatment, leaving said composition in contact with the hair and/or scalp and/or skin, and eventually rinsing it off.

* * * * *